(12) United States Patent
Chao et al.

(10) Patent No.: US 11,197,975 B2
(45) Date of Patent: Dec. 14, 2021

(54) LIGHT HEALTH CARE SYSTEM AND LIGHT HEALTH CARE METHOD

(71) Applicant: Industrial Technology Research Institute, Hsinchu (TW)

(72) Inventors: Wei-Cheng Chao, Kaohsiung (TW); Chi-Chin Yang, Hsinchu (TW); Li-Chi Su, Yilan County (TW); Mu-Tao Chu, Hsinchu (TW)

(73) Assignee: Industrial Technology Research Institute, Hsinchu (TW)

( * ) Notice: Subject to any disclaimer, the term of this patent is extended or adjusted under 35 U.S.C. 154(b) by 61 days.

(21) Appl. No.: 16/232,065

(22) Filed: Dec. 26, 2018

(65) Prior Publication Data
US 2019/0290882 A1    Sep. 26, 2019

Related U.S. Application Data

(60) Provisional application No. 62/646,379, filed on Mar. 22, 2018.

(30) Foreign Application Priority Data

Nov. 13, 2018   (TW) ................................ 107140149

(51) Int. Cl.
*A61M 21/02*     (2006.01)
*A61N 5/06*      (2006.01)
(Continued)

(52) U.S. Cl.
CPC .......... *A61M 21/02* (2013.01); *A61B 5/0022* (2013.01); *A61B 5/0205* (2013.01); *A61B 5/11* (2013.01);
(Continued)

(58) Field of Classification Search
CPC .............. A61M 21/00; A61M 21/02; A61M 2021/0005; A61M 2021/0044; A61N 5/0613; A61N 5/0618
See application file for complete search history.

(56) References Cited

U.S. PATENT DOCUMENTS 5,447,527 A * 9/1995 Waldman .............. A61M 21/00
607/88
6,053,936 A    4/2000 Koyama et al.
(Continued)

FOREIGN PATENT DOCUMENTS

CN   107106331    8/2017
CN   107439056    12/2017
(Continued)

OTHER PUBLICATIONS

"Office Action of Taiwan Counterpart Application," dated Jan. 31, 2020, p. 1-p. 8.

*Primary Examiner* — Carrie R Dorna
(74) *Attorney, Agent, or Firm* — JCIPRNET (57) ABSTRACT

A light health care system including a physiological sensing device, a processor, and a light source device is provided. The physiological sensing device is adapted to acquire physiological data of a user. The processor is coupled to the physiological sensing device, and the processor acquires at least one light parameter corresponding to the physiological data according to the physiological data. The light source device is coupled to the processor, and the light source device outputs a light beam according to the at least one light parameter, wherein a green light beam or a blue light beam in the light beam accounts for more than 40% of the light beam. A light health care method is also provided.

15 Claims, 7 Drawing Sheets

```
┌─────────────────────────────────────────────────────────┐
│       Acquiring physiological data of a user            │─ 710
└─────────────────────────────────────────────────────────┘
                            │
                            ▼
┌─────────────────────────────────────────────────────────┐
│  Acquiring at least one light parameter corresponding to│─ 720
│  the physiological data according to the physiological data│
└─────────────────────────────────────────────────────────┘
                            │
                            ▼
┌─────────────────────────────────────────────────────────┐
│ Outputting a light beam according to the at least one light│
│ parameter, light beam in the light beam accounts for more │─ 730
│             than 40% of the light beam                   │
└─────────────────────────────────────────────────────────┘
```

(51) Int. Cl.
*A61M 21/00* (2006.01)
*A61B 5/0205* (2006.01)
*A61B 5/11* (2006.01)
*A61B 5/16* (2006.01)
*A61B 5/00* (2006.01)
*A61B 5/318* (2021.01)
*A61B 5/369* (2021.01)
*A61B 5/024* (2006.01)
*A61B 5/08* (2006.01)

(52) U.S. Cl.
CPC .............. *A61B 5/165* (2013.01); *A61B 5/318* (2021.01); *A61B 5/369* (2021.01); *A61B 5/4812* (2013.01); *A61N 5/0618* (2013.01); *A61B 5/02405* (2013.01); *A61B 5/0816* (2013.01); *A61M 2021/0044* (2013.01); *A61N 2005/0626* (2013.01); *A61N 2005/0663* (2013.01)

(56) References Cited

U.S. PATENT DOCUMENTS

| | | | |
|---|---|---|---|
| 2004/0230252 A1* | 11/2004 | Kullok | A61M 21/00 607/48 |
| 2005/0073839 A1* | 4/2005 | Pederson | A61N 5/06 362/230 |
| 2012/0053395 A1* | 3/2012 | Witt | A61B 5/0482 600/27 |
| 2012/0330387 A1 | 12/2012 | Ferraz Rigo et al. | |
| 2016/0008568 A1* | 1/2016 | Attia | A61B 5/486 600/28 |
| 2017/0368367 A1* | 12/2017 | Sato | H05B 45/00 |

FOREIGN PATENT DOCUMENTS

| | | |
|---|---|---|
| CN | 107596533 | 1/2018 |
| TW | I293887 | 3/2008 |
| TW | 201235060 | 9/2012 |

\* cited by examiner

LIGHT HEALTH CARE SYSTEM AND LIGHT HEALTH CARE METHOD

CROSS-REFERENCE TO RELATED APPLICATION

This application claims the priority benefits of U.S. provisional application Ser. No. 62/646,379, filed on Mar. 22, 2018 and Taiwan application Ser. No. 107140149, filed on Nov. 13, 2018. The entirety of each of the above-mentioned patent applications is hereby incorporated by reference herein and made a part of this specification.

TECHNICAL FIELD

The disclosure relates to a health care system and a health care method, and relates to a light health care system and a light health care method.

BACKGROUND

Based on research results, about ¼ to ⅕ people worldwide have emotional problems or sleep problems. Emotional problems (e.g., depression) may become the biggest burden on health care, while sleep problems may cause negative impacts on mood, stress, heart or metabolism. At present, the emotional problems and sleep problems of the patient are mainly solved by adopting medical treatments. However, about 38% of medical treatments are ineffective for depression. In addition, medicines often cause side effects, such as the possibility of reducing the patient's ability to control the body, causing other diseases or increasing mortality. Moreover, medicines may interact with food, resulting in side effects, reduced speed of the body's decomposition of medicines, or the production of toxins. Therefore, medical treatments can easily cause inconvenient diet.

SUMMARY

The disclosure provides a light health care system and a light health care method, which can effectively solve, record and track emotional problems or sleep problems under the premise of fewer side effects and less restricted diet.

The light health care system in an embodiment of the disclosure includes a physiological sensing device, a processor and a light source device. The physiological sensing device is adapted to acquire physiological data of a user. The processor is coupled to the physiological sensing device, and the processor acquires at least one light parameter corresponding to the physiological data according to the physiological data. The light source device is coupled to the processor, and the light source device outputs a light beam according to the at least one light parameter, wherein a green light beam or a blue light beam in the light beam accounts for more than 40% of the light beam.

The light health care method in an embodiment of the disclosure includes the following steps. Physiological data of a user is acquired. At least one light parameter corresponding to the physiological data is acquired according to the physiological data. A light beam is output according to the at least one light parameter, wherein a green light beam or a blue light beam in the light beam accounts for more than 40% of the light beam.

To make the above features and advantages of the present disclosure more comprehensible, several embodiments accompanied with drawings are described in detail as follows.

BRIEF DESCRIPTION OF THE DRAWINGS

The accompanying drawings are included to provide a further understanding of the disclosure, and are incorporated in and constitute a part of this specification. The drawings illustrate embodiments of the disclosure and, together with the description, serve to explain the principles of the disclosure.

FIG. 6A to FIG. 6D are four schematic diagrams of a light source device.

DETAILED DESCRIPTION

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

In the following embodiments, wordings used to indicate directions, such as "up," "down," "front," "back," "left," and "right", merely refer to directions in the accompanying drawings. Therefore, the directional wording is used to illustrate rather than limit the disclosure. In the accompanying drawings, each drawing illustrates the general features of the methods, structures, and/or materials used in the specific exemplary embodiments. The drawings should not be construed as definition or limitation to the scope and property coveted by the specific exemplary embodiments. For instance, relative thicknesses and locations of film layers, regions or structures may be reduced or enlarged for clarity.

Figure 1:
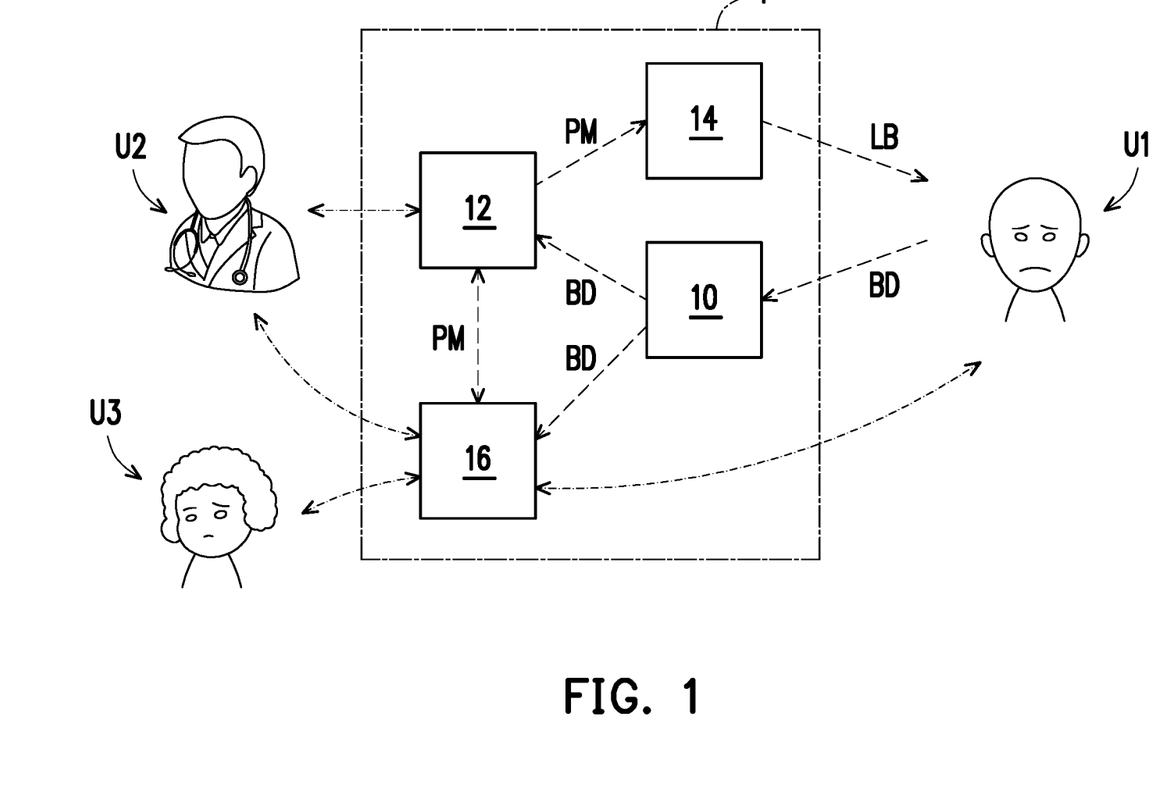
FIG. 1 is a schematic diagram of a light health care system according to an embodiment of the disclosure.

FIG. 1 is a schematic diagram of a light health care system according to an embodiment of the disclosure. With reference to FIG. 1, a light health care system 1 includes a physiological sensing device 10, a processor 12 and a light source device 14.

The physiological sensing device 10 is adapted to acquire physiological data BD of a user U1. For instance, the physiological sensing device 10 may include an electroencephalograph (EEG) sensing device, an electrocardiography (ECG) sensing device, a movement sensing device, a respiratory sensing device, or a combination of at least two of the above. Correspondingly, the physiological data BD may include an EEG, a heart rate, a heart rate variability (HRV), a body displacement, a respiratory frequency, or a combination of at least two of the above.

Figure 2:
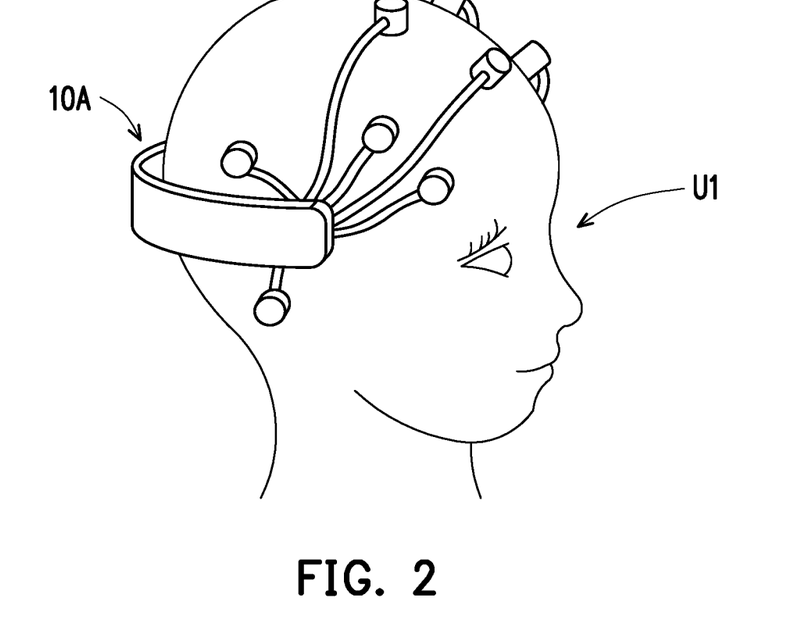
FIG. 2 is a schematic diagram of an EEG sensing device.

FIG. 2 is a schematic diagram of an EEG sensing device. With reference to FIG. 2, the physiological sensing device 10 of FIG. 1 may be an EEG sensing device 10A depicted in FIG. 2. The EEG sensing device 10A may be disposed on the head of the user U1 to acquire an electroencephalogram of the user U1. It should be noted that, the EEG sensing device 10A depicted in FIG. 2 is only one implementation type of the EEG sensing device. The specific type of the EEG sensing device may be changed as needed, and is not limited to the one shown in FIG. 2.

Figure 3:
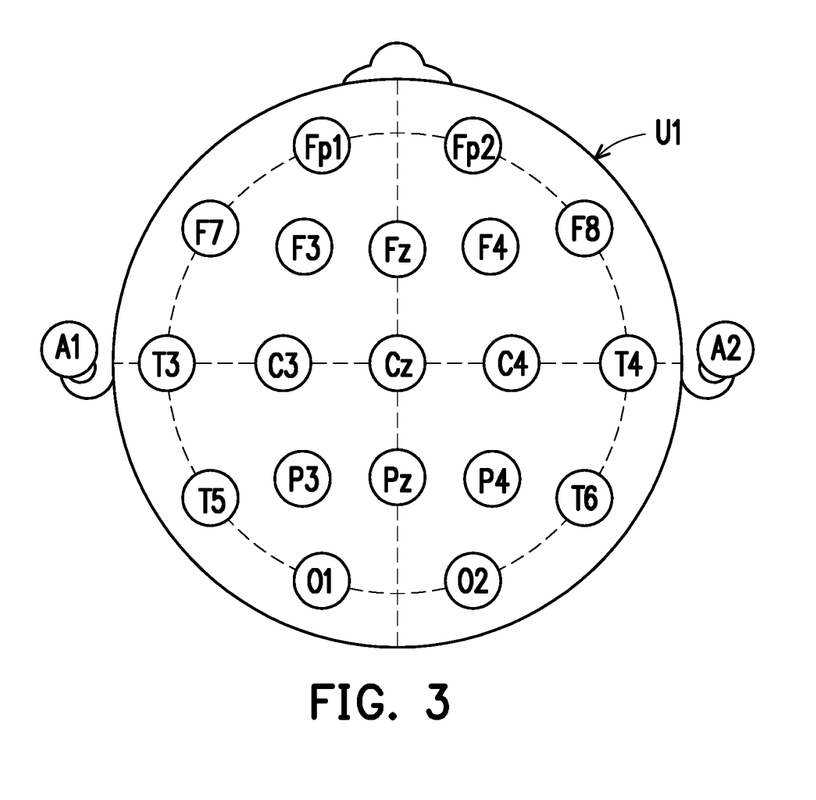
FIG. 3 is a schematic diagram of an electrode arrangement for acquiring an electroencephalograph (EEG).

FIG. 3 is a schematic diagram of an electrode arrangement for acquiring an electroencephalograph (EEG). With reference to FIG. 3, in the process of acquiring the EEG of the user U1, paired electrodes are placed on the head and the ears (in areas A1 and A2) of the user U1, so as to record brain wave indicators on a frontal lobe region (including areas Fp1, Fp2, F3, F4, Fz, F7 and F8), a temporal lobe region (including areas T3, T4, T5 and T6), a parietal lobe region (including areas P3, P4 and Pz), an occipital lobe region (including areas O1 and O2) and a central sulcus region (including areas C3, C4 and Cz) on the cerebral cortex. The brain wave indicators may include at least one of $\delta$ wave, $\theta$ wave, $\alpha$ wave, $\beta$ wave and $\gamma$ wave, but not limited thereto.

Different brain wave indicators indicate different states of the human body. Therefore, the states of the user U1 (e.g., an emotional state, a mental state or a sleep state) can be known by observing at least one of the brain wave indicators of at least one region on the cerebral cortex of the user U1 through the EEG. Here, the emotional state generally refers to psychological or physiological feelings of the user U1, such as relaxed, pleased, energetic, concentrated, awake or a combination of at least two of the above, but not limited thereto. The mental state generally refers to psychotherapy issues, such as mental problems including depression, seasonal affective disorder (SAD), generalized anxiety disorder (GAD), Alzheimer's disease (AD), Parkinson's disease (PD) or attention deficit hyperactivity disorder (ADHD), but not limited thereto. The sleep state generally refers to sleep quality issues and sleep phase issues. The sleep quality issues may include shortening a fall-asleep time, reducing the number of wake-ups, increasing a total sleep time, improving a sleep efficiency or soothing insomnia, but not limited thereto. The sleep phase issues may include issues like delayed sleep phase disorder (DSPD), advanced sleep phase disorder (ASPD), shift work disorder (SWD) or jet lag.

Figure 4:
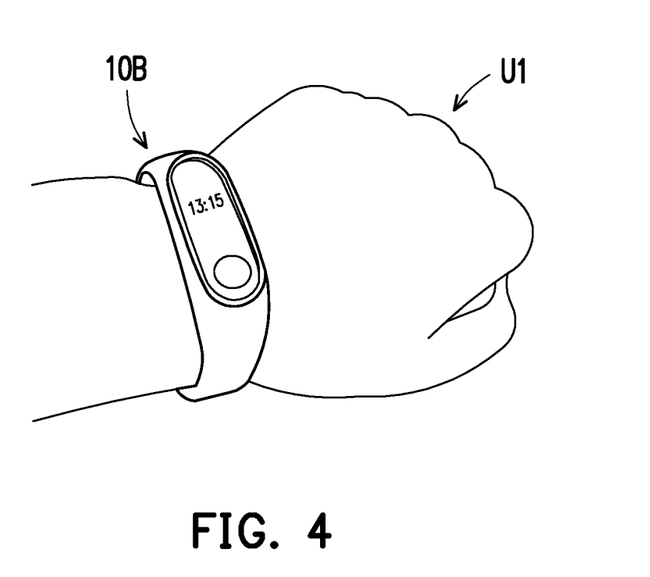
FIG. 4 is a schematic diagram of an electrocardiogram (ECG) sensing device.

FIG. 4 is a schematic diagram of an electrocardiogram (ECG) sensing device. With reference to FIG. 4, the physiological sensing device 10 of FIG. 1 may be an ECG sensing device 10B depicted in FIG. 4. The ECG sensing device 10B may be disposed on the wrist of the user U1 to acquire a heart rate, a heart rate variability or a combination of the two. It should be noted that, the ECG sensing device 10B depicted in FIG. 4 is only one implementation type of the ECG sensing device. The specific type of the ECG sensing device may be changed as needed, and is not limited to the one shown in FIG. 4.

The heart rate variability may include a time-domain analysis indicator and a frequency-domain analysis indicator calculated according to the heart rate variability. The time-domain analysis indicator may include standard deviation of normal to normal (SDNN) intervals, and the frequency-domain analysis indicator may include low frequency (LF), high frequency (HF) and low frequency to high frequency ratio (LF/HF). However, the disclosure is not limited in this regard.

SDNN represents the degree of autonomic nervous strength. Table 1 shows SDNN corresponding to different age groups. Under normal circumstances, the age is inversely proportional to SDNN. In other words, younger people have higher SDNN; older people have weaker SDNN. SDNN may serve as an indicator for determining whether a person is prematurely senile, as well as an indicator for determining whether an anti-disease treatment is effective to a patient.

LF refers to a physiological electric wave with frequency from 0.040 Hz to 0.150 Hz, which is an electric wave during the sympathetic discharge and represents sympathetic activity. HF refers to a physiological electric wave with frequency from 0.15 Hz to 0.400 Hz, which is an electric wave during the parasympathetic discharge and represents parasympathetic activity. LF/HF is a ratio of sympathetic and parasympathetic activities, which represents a balance of autonomic nervous activity. People of different ages have corresponding standard average of LF, HF and LF/HF. For example, at 21 to 40 years old, males have higher sympathetic (LF) than females, while females have higher parasympathetic (HF) than males. At 41 to 60 years old, males have higher parasympathetic (HF) than females. For males and females over 60 years old, the difference between LF and HF becomes smaller. In other words, LF/HF ratio decreases as the age increases With reference to FIG. 1, the processor 12 is coupled to the physiological sensing device 10, and the processor 12 acquires at least one light parameter PM corresponding to the physiological data BD according to the physiological data BD. For instance, the processor 12 may include a central processing unit (CPU) or a graphic processing unit (GPU), but not limited thereto.

Figure 5:
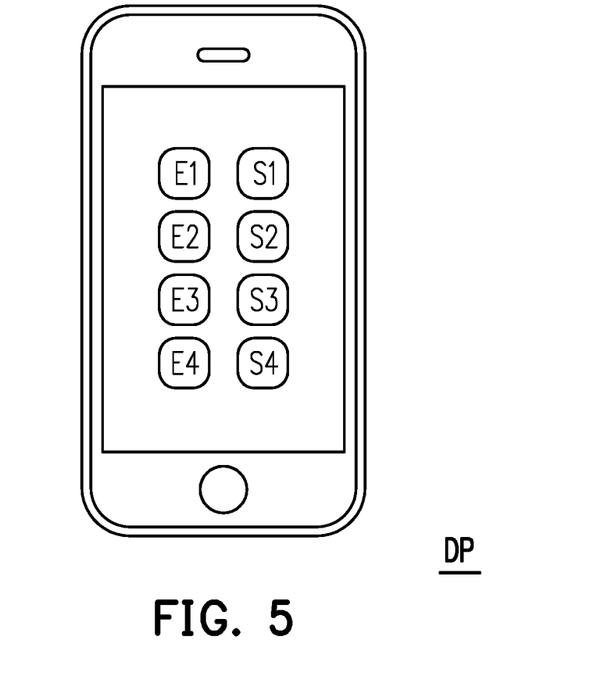
FIG. 5 is a schematic diagram of a display device.

FIG. 5 is a schematic diagram of a display device. With reference to FIG. 1 and FIG. 5, the processor 12 of the light health care system 1 may be inbuilt in the display device DP, but not limited thereto. The processor 12 and the physiological sensing device 10 may be connected in a wired or wireless manner for signal transmission. The processor 12 can store, calculate and analyze the physiological data BD. The processor 12 can determine the sleep state, the emotional state or the combination of the two of the user U1 according to the physiological data BD (e.g., the heart rate, the heart rate variability, the EEG, the body displacement, the respiratory frequency or the combination of at least two of the above). After determining the sleep state, the emotional state or the combination of the two of the user U1, the processor 12 acquires the at least one light parameter PM corresponding to the physiological data BD, and outputs the at least one light parameter PM to the light source device 14 so the light source device 14 can output a light beam LB corresponding to the at least light parameter PM to adjust the sleep state, the emotional state or the combination of the two of the user U1 through irradiation of the light beam LB. The at least one light parameter PM may include an irradiation duration, an irradiation timing, an irradiation type, a green light proportion, a blue light proportion, a color rendering index (CRI), or a combination of at least two of the above. Here, the irradiation duration refers a total time spent for each light health care. The irradiation timing refers to a time point of use of the light health care, such as use before bed, use within a period of time after wake up, etc. The irradiation type includes a monochromatic light and a mixed light. The green light proportion refers to the percentage by which the green light beam in the light beam LB accounts for spectrum of the light beam LB. Similarly, the blue light proportion refers to the percentage by which the blue light beam in the light beam LB accounts for spectrum of the light beam LB.

The processor 12 may be inbuilt with a plurality of algorithms for adjusting the emotional state and the sleep state of the user U1, and the display device DP may display a plurality of icons corresponding to the different emotional states and sleep states for the user U1 to select. In this embodiment, the processor 12 is in-built with algorithms for adjusting/improving four emotional states and four sleep states of the user U1, and the display device DP may display four icons corresponding to the four emotional states (e.g., icons E1, E2, E3 and E4) and four icons corresponding to the four sleep states (e.g., icons S1, S2, S3 and S4).

For instance, the icon E1 corresponds to the problem of stress. The user U1 may tap on the icon E1 to start the corresponding light health care functions (e.g., including steps for acquiring, storing, calculating the physiological data as well as for irradiation), thereby achieving the effect of relieving stress. The icon E2 corresponds to the problem of fatigability. The user U1 may tap on the icon E2 to start the corresponding light health care functions, thereby achieving the effect of boosting spirit (enhancing vitality). The icon E3 corresponds to the problem of inattention. The user U1 may tap on the icon E3 to start the corresponding light health care functions, thereby achieving the effect of improving concentration. The icon E4 corresponds to the problem of bad mood or negative emotion. The user U1 may tap on the icon E4 to start the corresponding light health care functions, thereby achieving the effect of improving positive emotions, suppressing depression or even soothing depression. The icon S1 corresponds to the problem of poor sleep quality. Poor sleep quality includes situations like frequent difficulty falling asleep, insomnia, insufficient deep sleep, and insufficient total sleep hours (being easily awakened). The user U1 may tap on the icon S1 to start the corresponding light health care functions (e.g., including steps for acquiring, storing, calculating the physiological data as well as for irradiation), thereby achieving the effect of improving sleep quality. The icon S2 corresponds to the problem of delayed sleep phase disorder (DSPD). DSPD includes problems like "inability to fall asleep before 2 AM and inability to get up normally in the morning" and dim light melatonin onset (DLMO). The user U1 may tap on the icon S2 to start the corresponding light health care functions, thereby achieving the effect of relieving DLMO. The icon S3 corresponds to the problem of advanced sleep phase disorder (ASPD). ASPD includes problems like "feeling sleepy at 6 PM, waking up around 2 AM and then difficult to continue to sleep to the morning" and DLMO. The user U1 may tap on the icon S3 to start the corresponding light health care functions, thereby achieving the effect of relieving ASPD. The icon S4 corresponds to the problem of difficulty falling asleep. The user U1 may tap on the icon S4 to start the corresponding light health care functions, thereby achieving the effect of enhancing sleepiness.

It should be noted that, the type and the number of states to be improved for the user may be changed as needed, and is not limited by those shown in FIG. 5.

With reference to FIG. 1, the light source device 14 is coupled to the processor 12, and the light source device 14 outputs the light beam LB according to the at least one light parameter PM, wherein a green light beam or a blue light beam in the light beam LB accounts for more than 40% of the light beam LB. For instance, the light source device 14 may include at least one red light emitting element, at least one green light emitting element, at least one blue light emitting element and at least one yellow light emitting element to mix white light required. The light emitting elements are, for example, light emitting diodes, but not limited thereto. A proportion of a particular monochromatic light (e.g., at least one of green light and blue light) in white light (a ratio of a light intensity of green/blue light to a light intensity of white light) may be adjusted to make the user produce particular physiological reaction and biological effect, thereby achieving the effects of adjusting or improving the emotional state and/or the sleep state or staying healthy. In an embodiment, the light source device 14 may be a monochromatic light emitting element with phosphor or a monochromatic light emitting element with quantum dot to mix white light. Alternatively, the light source device 14 may also be another type of white light source with a filter module (including a filter).

Figure 6A:
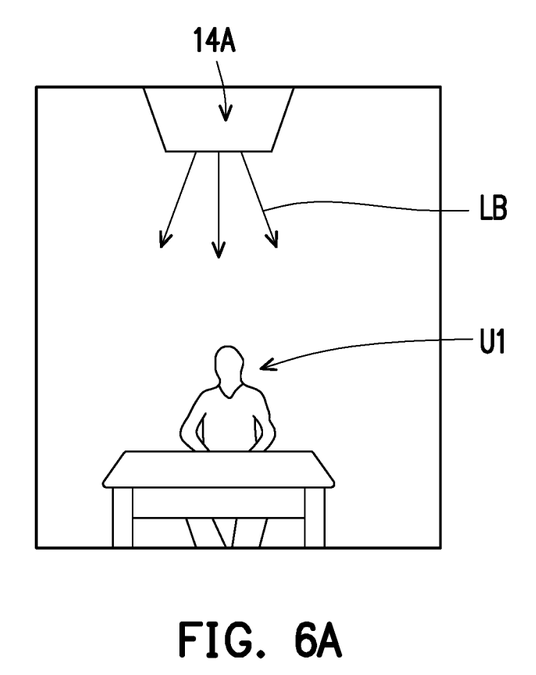

FIG. 6A to FIG. 6D are four schematic diagrams of a light source device. With reference to FIG. 6A, the light source device 14 of FIG. 1 may be a lamp 14A adapted to provide a larger illumination range shown in FIG. 6A, such as a fluorescent lamp or a desk lamp. Under this architecture, the light beam LB provided by the lamp 14A is, preferably, white light. White light may be adjusted into an optimal light source recipe (e.g., the green light proportion, the blue light proportion and the color rendering index range) according to a light source application purpose. In this way, discomfort or interference of the user or other person in the same space can be reduced to an acceptable or undetected extent while adjusting or improving the emotional state and/or the sleep state or staying healthy. In addition, under the architecture that adopts the fixed lamp 14A, since it is possible to choose the place where the lamp 14A is placed, the user U1 does not go to the clinic or hospital for the light health care.

Figure 6B:
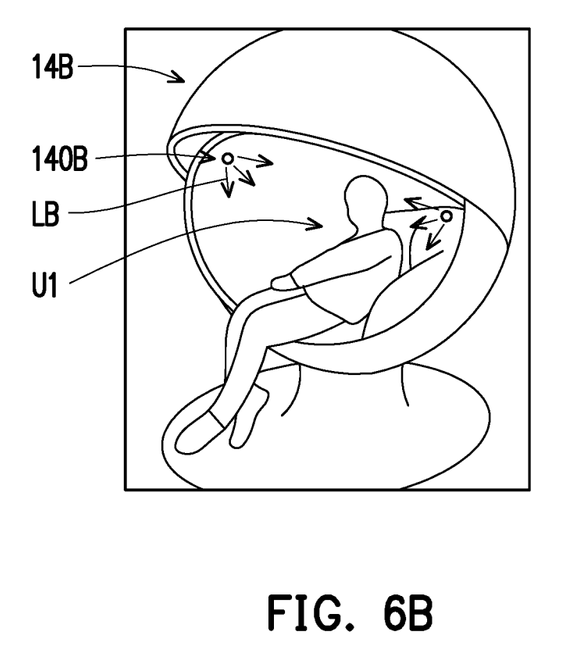

With reference to FIG. 6B, the light source device 14 of FIG. 1 may be a capsule 14B adapted to provide irradiation within a defined range as shown in FIG. 6B. A light emitting element 140B is disposed in the capsule 14B to provide the light beam LB.

Figure 6C:
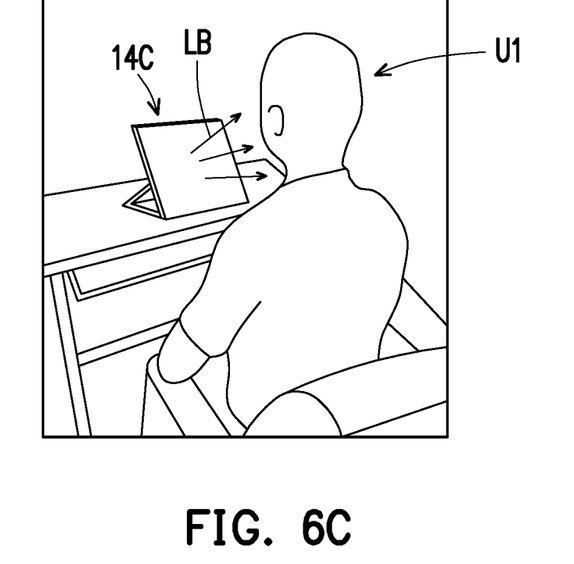

With reference to FIG. 6C, the light source device 14 of FIG. 1 may be a portable light source device 14C shown in FIG. 6C, which is easy to carry for the user U1. In this way, the user U1 can use the light health care about anywhere.

Figure 6D:
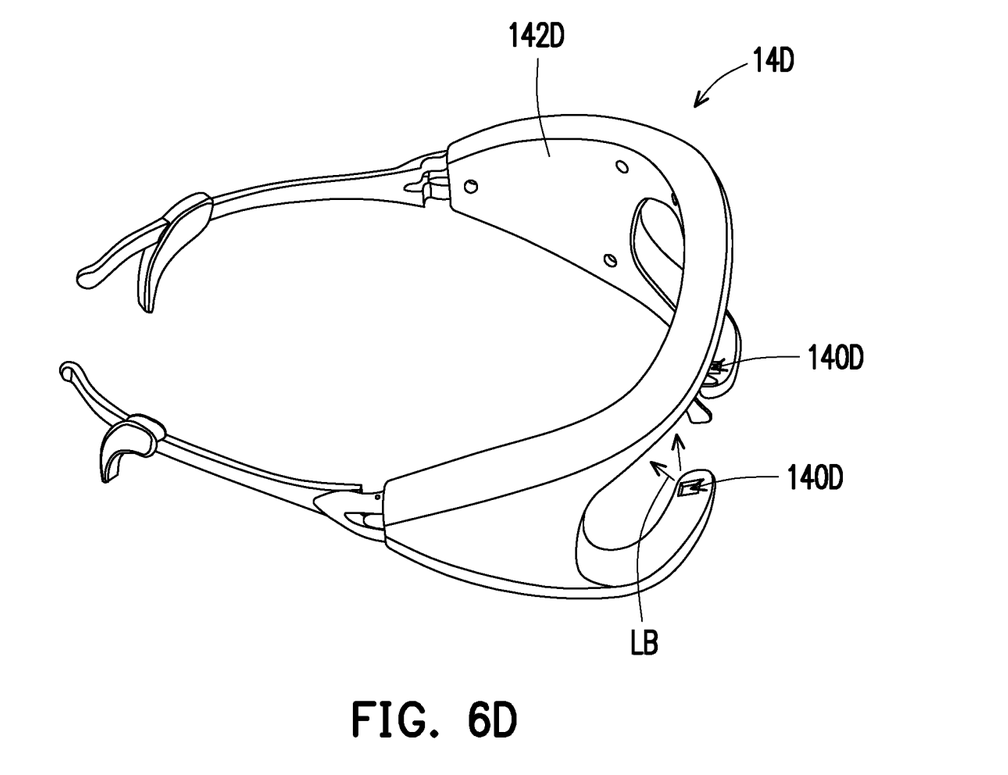

With reference to FIG. 6D, the light source device 14 of FIG. 1 may be a wearable light source device 14D shown in FIG. 6D. A light emitting element 140D in the wearable light source device 14D can be arranged around the user's eye by a fixing element 142D so that the light beam LB emitted from the light emitting element 140D does not significantly affect the user's line of sight. Accordingly, visual and psychological influences of the light beam LB emitted by the light emitting element 140D may be reduced for the user. Thus, it only needs to consider a physiological effect (generally referring to a common physiological reaction such as the heart rate and the EEG response) and a biological effect (generally referring to hormone secretion changes, where hormone may include melatonin, γ-Aminobutyric acid (GABA), cortisol, dopamine, serotonin, norepinephrine, endorphin, oxytocin and acetylcholine) caused by the light beam LB on the user LB. In this case, the light beam LB may not be white light. For instance, a light emitting element 140D in the light source device 14D may not include a red light emitting element but only includes at least one of a green light emitting element and a blue light emitting element. In addition, under the architecture that adopts the wearable light source device, the user can use the light health care about anywhere.

With reference to FIG. 1, according to different needs, the light health care system 1 may further include other elements and/or devices. For instance, the light health care system 1 may further include a cloud database 16. The cloud database 16 may be coupled to the physiological sensing device 10 and the processor 12 to store the physiological data BD and the light parameter PM used.

A doctor U2 and the user U1 may determine whether the emotional state and/or the sleep state of the user U1 are improved according to the physiological data BD stored in the cloud database 16. Moreover, the doctor U2 may conduct diagnosis based on the physiological data BD stored in the cloud database 16 and accordingly adjust the optimal light source recipe (e.g., the green light proportion, the blue light proportion and the color rendering index range). In addition, under the authorization of the user U1, a family member U3 of the user U1 may also check the physiological data BD stored in the cloud database 16 to know the emotional state and/or the sleep state of the user U1 and sent out caring messages in time.

Figure 7:
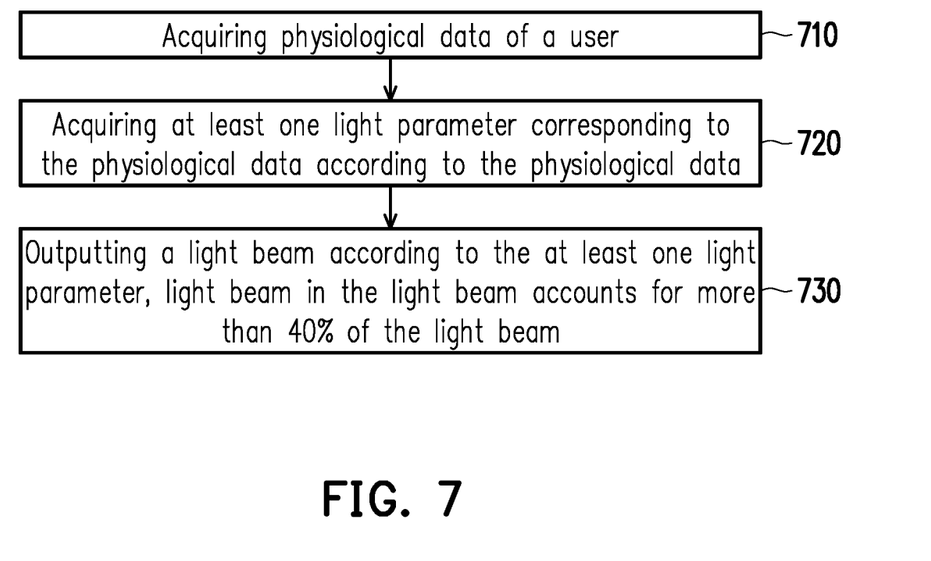
FIG. 7 is a flowchart of a light health care method according to an embodiment of the disclosure.

FIG. 7 is a flowchart of a light health care method according to an embodiment of the disclosure. With reference to FIG. 7, in step 710, physiological data of a user is acquired. For instance, a brain wave, a heart rate, a heart rate variability, an EEG, a body displacement, a respiratory frequency or a combination of at least two of the above may be acquired by using the EEG sensing device, the ECG sensing device, the movement sensing device, the respiratory sensing device, or the combination of at least two of the above.

In step S720, at least one light parameter corresponding to the physiological data is acquired according to the physiological data. Specifically, an emotional state and/or a sleep state of the user may be determined according to the physiological data, and then an optimal light source recipe corresponding thereto (e.g., an irradiation duration, an irradiation timing, an irradiation type, a green light proportion, a blue light proportion, a color rendering index, or a combination of at least two of the above) may be confirmed.

In step 730, a light beam is output according to the at least one light parameter, wherein a green light beam or a blue light beam in the light beam accounts for more than 40% of the light beam. Specifically, a proportion of a particular monochromatic light (e.g., at least one of green light and blue light) in white light may be adjusted to make the user produce particular physiological reaction and biological effect, thereby achieving the effects of adjusting or improving the emotional state and/or the sleep state or staying healthy.

Taking the emotional state as an example, the emotional state of the user may be determined according to the heart rate variability. Table 1 lists emotional problems, improvement goals, determination indicators and optimal light source recipes of the user. In Table 1, as long as at least one of the determination indicators is true, the corresponding optimal light source recipe may be used to make progress on solving the emotional problems. When the user has more than one of the emotional problems, the processor may calculate the corresponding optimal light source recipe (e.g., a union of the optimal light source recipes) so as to make progress on solving on various emotional problems at the same time. Among the optimal light source recipes, the irradiation duration, the light source type (the monochromatic light or the mixed light) and the color rendering index are considered together as a whole, wherein only one of the monochromatic light and the mixed light is selected as the light source type for the light health care. Taking the problem of fatigability as an example, when the monochromatic light is selected for the light health care, the light beam LB in FIG. 1 is green light, and the green light beam in the light beam LB accounts for 100% of the light beam LB. On the other hand, when the mixed light is selected for the light health care, the light beam LB in FIG. 1 is white light, and the green light beam in the light beam LB accounts for more than 40% of the light beam LB.

TABLE 1

| | Emotional state | | | |
|---|---|---|---|---|
| Problems | Stress | Fatigability | Inattention | Bad mood/ Negative emotion |
| Improvement goals | Relieving stress | Boosting spirit/ Enhancing vitality | Improving concentration | Pleasing |
| Determination indicators | 1. SDNN lower than the standard average of the user's age<br>2. LF/HF higher than the standard average of the user's age | 1. SDNN lower than the standard average of the user's age group<br>2. [LF + HF] lower than the standard average of [LF + HF] of the user's age | 1. LF higher than the standard average of the user's age<br>2. LF/HF higher than the standard average of the user's age | 1. SDNN lower than the standard average of the user's age<br>2. LF/HF higher than the standard average of the user's age<br>3. LF higher than or HF lower than the standard average of the user's age |
| Optimal light source recipes | Irradiation duration: more than 0.5 hours<br>Monochromatic light: green light<br>Mixed light: green light accounting for more than 40% of white light, and blue light accounting for less than 5% of white light<br>(CRI ≥ 70) | Irradiation duration: more than 0.5 hours<br>Monochromatic light: green light<br>Mixed light: green light accounting for more than 40% of white light<br>(CRI ≥ 70) | Irradiation duration: more than 0.5 hours<br>Monochromatic light: green light<br>Mixed light: green light accounting for more than 40% of white light, and red light accounting for more than 10% of white light<br>(CRI ≥ 70) | Irradiation duration: more than 0.5 hours<br>Monochromatic light: green light<br>Mixed light: green light accounting for more than 40% of white light, and blue light accounting for more than 10% of white light<br>(CRI ≥ 70) |

Taking the sleep state as an example, the sleep state of the user may be determined according to the EEG, the heart rate, the heart rate variability, the body displacement, the respiratory frequency or the combination of at least two of the above. Measurement items for observing the sleep state may include a fall-asleep time, a wake-up time, a deep sleep time, the number of wake-ups per night, a total sleep time (TST), a sleep efficiency (SE) and/or a sleep latency, but not limited thereto. Here, the sleep efficiency=(an actual sleeping time/a total time in bed)*100%. The sleep latency is defined as the time from lying down to falling asleep.

For instance, the number of wake-ups per night of the user may be observed by the movement sensing device (e.g., actigraphy), and sleep conditions of the user may be observed by the ECG and/or the EEG. Specifically, a maximum heart rate of the user in an awake state is equal to 208−(0.7*the user's age). When the user falls asleep, the maximum heart rate of the user is reduced by 14 bpm (for users over 60 years old) to 24 bpm (for young people). When people are sleeping, LF/HF ratio will be reversed (i.e., HF is higher and the ratio is lower than 1), and it is difficult to get to the deep sleep if LF/HF ratio is still greater than 1 when sleeping. Therefore, whether the user falls asleep or not may be determined by observing the maximum heart rate of the user, and accordingly, the fall-asleep time, the wake-up time, the number of wake-ups per night, the total sleep time, the sleep efficiency and/or the sleep latency may then be calculated. On the other hand, because the brain wave indicators of the user changes with different sleep stages (e.g., awake stage, non-rapid eye movement stage and rapid eye movement stage), the deep sleep time of the user may be calculated by observing the brain wave indicators (e.g., δ wave, θ wave, α wave and β wave) of the different areas on the cerebral cortex (e.g., area C3, area C4 and area O1).

In an embodiment, the sleep state of the use may be observed for seven consecutive days so the optimal light source recipe may be determined according to the sleep state of the user in these seven days. In other words, the optimal light source recipe for an X-th day is determined by the sleep state from an (X−1)-th day to an (X−7)-th day, but not limited thereto. For instance, if the goal is enhancing sleepiness, the light health care may be performed by adopting the corresponding optimal light source recipe directly.

Table 2 lists sleep problems, improvement goals, determination indicators and optimal light source recipes. In Table 2, as long as at least one of the determination indicators is true, the corresponding optimal light source recipe may be used to make progress on solving the sleep problems. When the user has more than one of the sleep problems or when the user has both the sleep and emotional problems, the processor may calculate the corresponding optimal light source recipe (a union of the optimal light source recipes) so as to make progress on solving various problems at the same time. Among the optimal light source recipes, the irradiation timing, the irradiation duration, the light source type (the monochromatic light or the mixed light) and the color rendering index are considered together as a whole, wherein only one of the monochromatic light and the mixed light is selected as the light source type for the light health care.

TABLE 2

| | Sleep state | | | |
|---|---|---|---|---|
| Problems | Frequent difficulty falling asleep Insomnia Insufficient deep sleep Insufficient total sleep hours (being easily awakened) | Inability to fall asleep before 2AM and inability to get up normally in the morning | Feeling sleepy at 6PM, waking up around 2AM and then difficult to continue to sleep to the morning | Frequent difficulty falling asleep |
| Improvement goals | Improving sleep quality | Relieving DSPD | Relieving ASPD | Enhancing sleepiness |
| Determination indicators | 1. Sleep latency > 0.5 hours 2. The number of wake-ups per night > 3 3. Total sleep time < 6 hours (15 to 85 years old) 4. Sleep efficiency < 80% | Falling asleep after 2AM and waking up after 10AM for more than 4 days per week | Feeling sleepy around 7PM and waking up around 2AM for more than 4 days per week | Sleep latency > 0.5 hours |
| Optimal light source recipes | Irradiation timing: within 2 hours after wake up Irradiation duration: more than 0.5 hours Monochromatic light: green light Mixed light: green light accounting for more than 40% of white light (CRI ≥ 70) | Irradiation timing: within 2 to 3 hours after wake up Irradiation duration: more than 1 hour Monochromatic light: green light Mixed light: green light accounting for more than 40% of white light (CRI ≥ 70) | Irradiation timing: 7 to 9PM Irradiation duration: 1 hour Monochromatic light: blue light Mixed light: blue light accounting for more than 40% of white light (CRI ≥ 70) | Irradiation timing: before bed Monochromatic light: green light Mixed light: green light accounting for more than 50% of white light, and blue light accounting for less than 5% of white light (CRI ≥ 70) |

In Table 1 and Table 2, when the mixed light is adopted for the light health care, a proportion of the monochromatic light in white light affects color temperature of white light and irradiance of the monochromatic light entering the user's eye. In addition, as can be known from human factor experiments, under different combinations of color temperature-illuminance, the user would have different visual and psychological feelings, such as "glaring and not glaring", "nervous and relaxed", "sleepy and awake", "depressed and pleased", "discomfort and comfort" and "cold and warm", but not limited thereto. Accordingly, the visual and psychological feelings of the user may be taken into consideration for adjusting color temperature and illuminance in the optimal light source recipe.

Figure 8:
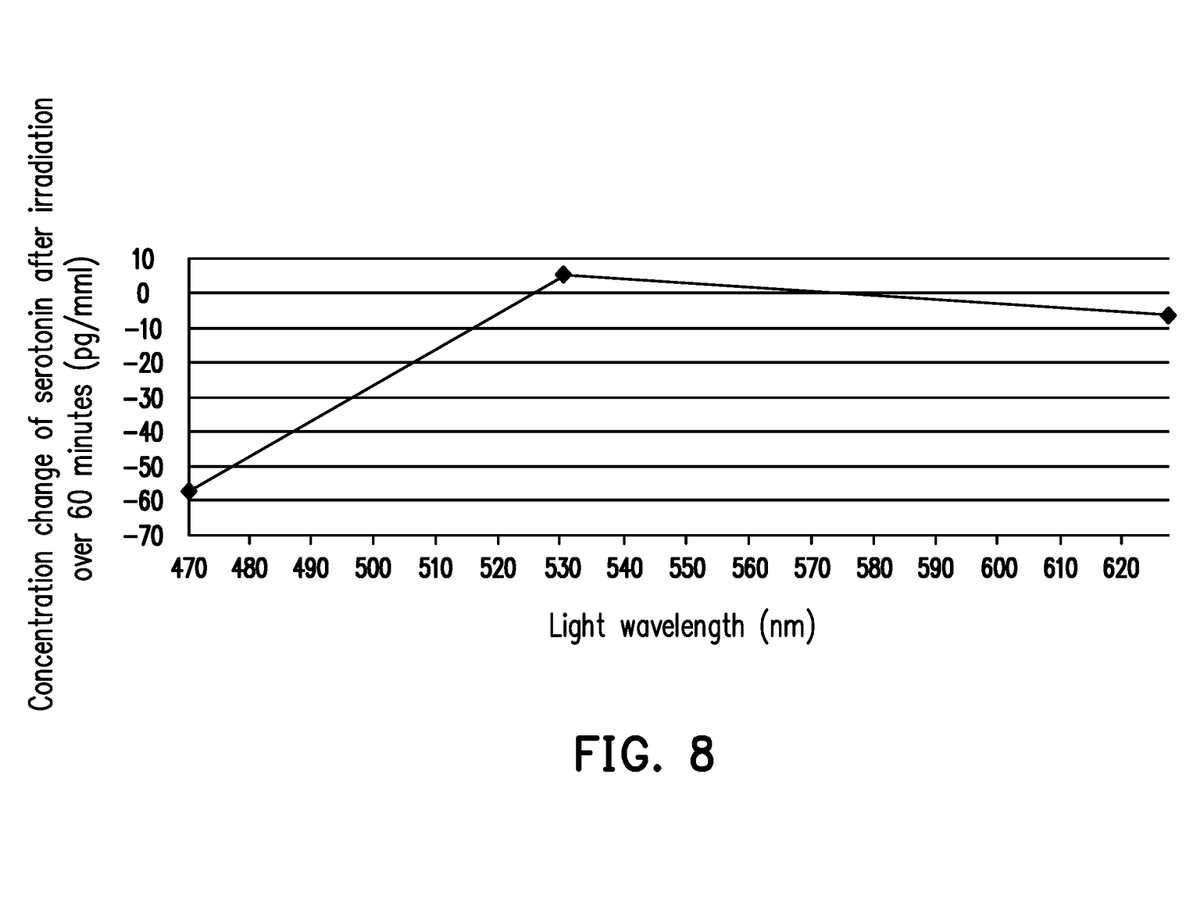
FIG. 8 is a graph showing the relationship between concentration change of serotonin and light wavelength.

For the biological effect of light on the human body, changes in sleep-related hormones (e.g., melatonin and serotonin) and emotion-related hormones (e.g., γ-Aminobutyric acid (GABA), cortisol, dopamine, serotonin, norepinephrine, endorphin, oxytocin and acetylcholine) in the blood may be collected and analyzed before and after an experiment in which the human body is exposed to irradiation of the monochromatic lights (red, blue, green, etc.) and a cool white light from a common lighting T5 tubes for 60 minutes, and then an action spectrum of the light source to each hormone may be established. FIG. 8 is a graph showing the relationship between concentration change of serotonin and light wavelength. According to the users' situation, a suitable wavelength may be selected for the user in the light health care with reference to FIG. 8, but not limited thereto.

In addition, the biological effect of the user may also be taken into consideration for establishing a combined light source with optimized color temperature, illuminance and spectrum that can simultaneously satisfy requirements of the visual, psychological, physiological and biological effects for the user. For instance, a viable range of wavelength and intensity of an irradiating light may first be confirmed based on the physiological effect and the biological effect, and then a viable range of color temperature and illuminance may be confirmed based on a visual effect (visual comfort) and a psychological effect (pleasing). The physiological effect may include (but not limited to): a blue light irradiation that makes Ln(F4)−Ln(F3)>0, wherein Ln(F4) is a natural logarithm of α wave or θ wave power in area F4, area F8 and area Fp2 (referring to FIG. 3) in the frontal lobe region of the user, and Ln(F3) is a natural logarithm of α wave or θ wave power in area F3, area F7, and area Fp1 (referring to FIG. 3) in the frontal lobe region of the user. The biological effect may include (but not limited thereto): a green light irradiation that increases serotonin secretion.

In an embodiment, the optimal light source recipe for relieving stress may be changed from "mixed light: green light accounting for more than 40% of white light and blue light accounting for less than 5% of white light" in Table 1 to "mixed light: color temperature of white light ranged from 3,000 K to 4,500 K, illuminance of white light ranged from 400 lux to 800 lux, and irradiance (intensity) of green light entering the user's eye ≥30 µW/cm²".

In an embodiment, the optimal light source recipe for boosting spirit and/or enhancing vitality may be changed from "mixed light: green light accounting for more than 40% of white light" in Table 1 to "mixed light: color temperature of white light ranged from 4,500 K to 6,500 K, illuminance of white light ≥700 lux, irradiance (intensity) of green light entering the user's eye ≥30 µW/cm², irradiance (intensity) of blue light entering the user's eye ≥30 µW/cm², and irradiance of green light is greater than irradiance of blue light".

In an embodiment, the optimal light source recipe for improving concentration may be changed from "mixed light: green light accounting for more than 40% of white light, and red light accounting for more than 10% of white light" in Table 1 to "mixed light: color temperature of white light ranged from 4,500 K to 6,500 K, illuminance of white light ≥700 lux, irradiance (intensity) of green light entering the user's eye ≥30 µW/cm², irradiance (intensity) of blue light entering the user's eye ≥30 µW/cm², and irradiance of green light is greater than irradiance of blue light".

In an embodiment, the optimal light source recipe for pleasing, suppressing negative emotion and/or enhancing positive emotions for the user may be changed from "mixed light: green light accounting for more than 40% of white light and blue light accounting for more than 10% of white light" in Table 1 to "mixed light: color temperature of white light ranged from 4,500 K to 6,500 K, illuminance of white light ≥700 lux, irradiance (intensity) of blue light entering the user's eye ≥30 µW/cm²".

In an embodiment, the optimal light source recipe for improving sleep quality may be changed from "mixed light: green light accounting for more than 40% of white light" in Table 2 to "mixed light: color temperature of white light ≥5,000 K, illuminance of white light ≥700 lux, irradiance (intensity) of green light entering the user's eye ≥30 µW/cm², and irradiance (intensity) of blue light entering the user's eye ≥30 µW/cm²".

In an embodiment, the optimal light source recipe for relieving DSPD may be changed from "mixed light: green light accounting for more than 40% of white light" in Table 2 to "mixed light: color temperature of white light ≥5,000 K, illuminance of white light ≥700 lux, irradiance (intensity) of green light entering the user's eye ≥30 µW/cm², and irradiance (intensity) of blue light entering the user's eye ≥30 µW/cm²".

In an embodiment, the optimal light source recipe for relieving ASPD may be changed from "mixed light: blue light accounting for more than 40% of white light" in Table 2 to "mixed color: color temperature of white color ≥5,000 K, illuminance of white light ≥800 lux, and irradiance (intensity) of blue light entering the user's eye ≥30 µW/cm²".

In an embodiment, the optimal light source recipe for enhancing sleepiness may be changed from "mixed light: green light accounting for more than 50% of white light, and blue light accounting for less than 5% of white light" in Table 2 to "mixed light: color temperature of white light ranged from 3,000 K to 4,500 K, illuminance of white light ≤600 lux, irradiance (intensity) of green light entering the user's eye ≥30 µW/cm² and irradiance (intensity) of yellow light entering the user's eye ≥30 µW/cm²".

In summary, the light health care system and the light health care method of the resent disclosure can be used to acquire the physiological data of the user, determine the emotional state and/or the sleep state according to the physiological data, and perform the light health care according to the determination result. Since the light health care has smaller side effects and the light health care cannot easily interact with the food, the light health care system and the light health care method according to the embodiments of the present disclosure can make progress on solving the emotional problems and/or the sleep problems under the premise of less side effects and less restricted diet. In an embodiment, the light source device may adopt the portable light source device or the wearable light source device, which are easy to carry so the light health care can be used without being restricted by the size of the place and/or the space. In another embodiment, the physiological data and the light parameter may be stored in the cloud database, and the physiological data and the light parameter stored in the cloud database may be shared to the doctor and/or the family member of the user through the authorization of the user. In yet another embodiment, the visual and psychological feelings, the physiological and biological effects of the user may be taken into consideration for adjusting a combination of color temperature, illuminance and spectrum in the optimal light source recipe.

It will be apparent to those skilled in the art that various modifications and variations can be made to the disclosed embodiments. It is intended that the specification and examples be considered as exemplary only, with a true scope of the present disclosure being indicated by the following claims and their equivalents.

What is claimed is:
1. A light health care system, comprising:
a physiological sensing circuit, adapted to acquire physiological data of a user;
a processor, coupled to the physiological sensing circuit, the processor acquiring at least one light parameter corresponding to the physiological data according to the physiological data; and
a light source device, coupled to the processor, and outputting white light according to the at least one light parameter, wherein green light or blue light in the white light accounts for more than 40% of the white light, wherein an illuminance of the white light is larger than or equal to 700 lux, an irradiance of the blue light or an irradiance of the green light entering the user's eye is larger than or equal to 30 μW/cm$^2$, and the irradiance of green light is greater than the irradiance of blue light.

2. The light health care system according to claim 1, wherein the physiological sensing circuit comprises an EEG sensing circuit, an ECG sensing circuit, a movement sensing circuit, a respiratory sensing circuit, or a combination of at least two of the above.

3. The light health care system according to claim 1, wherein the physiological data comprises an EEG, a heart rate, a heart rate variability, a body displacement, a respiratory frequency, or a combination of at least two of the above.

4. The light health care system according to claim 3, wherein the heart rate variability comprises a time-domain analysis indicator and a frequency-domain analysis indicator calculated according to the heart rate variability.

5. The light health care system according to claim 3, wherein the processor is configured to determine an emotional state of the user according to the heart rate variability.

6. The light health care system according to claim 1, wherein the processor is configured to determine a sleep state of the user according to the physiological data acquired by the physiological sensing circuit, and the physiological data includes a heart rate, a heart rate variability, an EEG, a body displacement, a respiratory frequency or a combination of at least two of the above.

7. The light health care system according to claim 1, wherein the at least one light parameter comprises an irradiation duration, an irradiation timing, an irradiation type, a green light proportion, a blue light proportion, a color rendering index, or a combination of at least two of the above.

8. The light health care system according to claim 1, further comprising:
a cloud database, coupled to the physiological sensing circuit and the processor.

9. A light health care method, comprising:
acquiring physiological data of a user;
acquiring at least one light parameter corresponding to the physiological data according to the physiological data; and
outputting white light according to the at least one light parameter, wherein green light or blue light in the white light accounts for more than 40% of the white light, wherein an illuminance of the white light is larger than or equal to 700 lux, an irradiance of the blue light or an irradiance of the green light entering the user's eye is larger than or equal to 30 μW/cm$^2$, and the irradiance of green light is greater than the irradiance of blue light.

10. The light health care method according to claim 9, wherein the physiological data comprises an EEG, a heart rate, a heart rate variability, a body displacement, a respiratory frequency, or a combination of at least two of the above.

11. The light health care method according to claim 10, wherein the heart rate variability comprises a time-domain analysis indicator and a frequency-domain analysis indicator calculated according to the heart rate variability.

12. The light health care method according to claim 9, wherein the physiological data comprises a heart rate variability, and the white light is adapted to adjust an emotional state of the user.

13. The light health care method according to claim 9, wherein the physiological data comprises an EEG, a heart rate, a heart rate variability, a body displacement, a respiratory frequency or a combination of at least two of the above, and the white light is adapted to adjust a sleep state of the user.

14. The light health care method according to claim 9, wherein the at least one light parameter comprises an irradiation duration, an irradiation timing, an irradiation type, a green light proportion, a blue light proportion, a color rendering index, or a combination of at least two of the above.

15. The light health care method according to claim 9, further comprising:
storing the physiological data and the at least one light parameter.

* * * * *